(12) United States Patent
Fanous

(10) Patent No.: US 7,052,457 B2
(45) Date of Patent: May 30, 2006

(54) SELF-RETAINING RETRACTOR

(76) Inventor: Refaat S. Fanous, 4 Merrymount Dr., North Dartmouth, MA (US) 02747

( * ) Notice: Subject to any disclaimer, the term of this patent is extended or adjusted under 35 U.S.C. 154(b) by 256 days.

(21) Appl. No.: 10/616,707

(22) Filed: Jul. 10, 2003

(65) Prior Publication Data

US 2004/0059193 A1    Mar. 25, 2004

Related U.S. Application Data

(60) Provisional application No. 60/395,234, filed on Jul. 11, 2002.

(51) Int. Cl.
*A61B 1/32* (2006.01)

(52) U.S. Cl. ..................................... 600/220
(58) Field of Classification Search ................ 600/210, 600/215, 220, 226–228, 230–234; 128/898
See application file for complete search history.

(56) References Cited

U.S. PATENT DOCUMENTS

| | | | | |
|---|---|---|---|---|
| 497,064 A * | 5/1893 | Van Meter | ................... | 600/234 |
| 519,623 A * | 5/1894 | Wertheimer | ................ | 600/220 |
| 605,547 A * | 6/1898 | Holland | ....................... | 600/220 |
| 1,030,530 A * | 6/1912 | Palmer | ........................ | 600/220 |
| 1,157,202 A * | 10/1915 | Bates et al. | .................. | 600/208 |
| 1,707,689 A * | 4/1929 | Sloan | .......................... | 600/233 |
| 3,176,682 A | 4/1965 | Wexler | | |
| 3,384,078 A * | 5/1968 | Gauthier | ...................... | 600/215 |
| 3,509,873 A * | 5/1970 | Karlin et al. | ............... | 600/226 |
| 3,522,799 A | 8/1970 | Gauthier | | |
| 3,724,449 A | 4/1973 | Gauthier | | |
| 4,010,741 A * | 3/1977 | Gauthier | ...................... | 600/234 |
| 4,254,763 A | 3/1981 | McCready et al. | | |
| 5,299,563 A * | 4/1994 | Seton | ......................... | 600/215 |
| 6,024,697 A | 2/2000 | Pisarik | | |
| 6,083,154 A * | 7/2000 | Liu et al. | ..................... | 600/234 |
| 6,099,468 A * | 8/2000 | Santilli et al. | .............. | 600/232 |
| 6,234,961 B1 * | 5/2001 | Gray | ............................ | 600/234 |
| 6,264,605 B1 * | 7/2001 | Scirica et al. | ............... | 600/227 |
| 6,342,036 B1 | 1/2002 | Cooper et al. | | |

* cited by examiner

*Primary Examiner*—Eduardo C. Robert
*Assistant Examiner*—Michael J. Araj
(74) *Attorney, Agent, or Firm*—Bromberg & Sunstein LLP

(57) ABSTRACT

A disclosed retraction device for gynecological surgery on a patient comprises, in one embodiment according to the invention, a frame hinged on a handle, the frame comprising a track; and at least one retractor slidably mounted on the track by a jig that does not contact the patient. The retraction device may be capable of being retained in position for surgery by the weight of the patient.

7 Claims, 10 Drawing Sheets

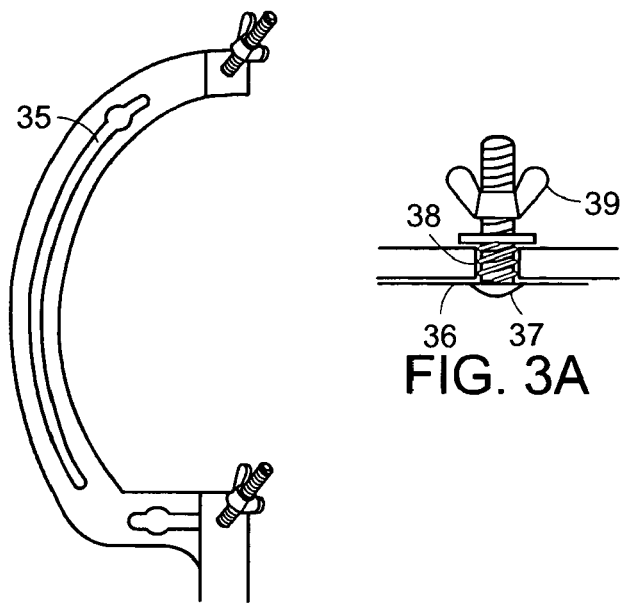
FIG. 3
FIG. 3A
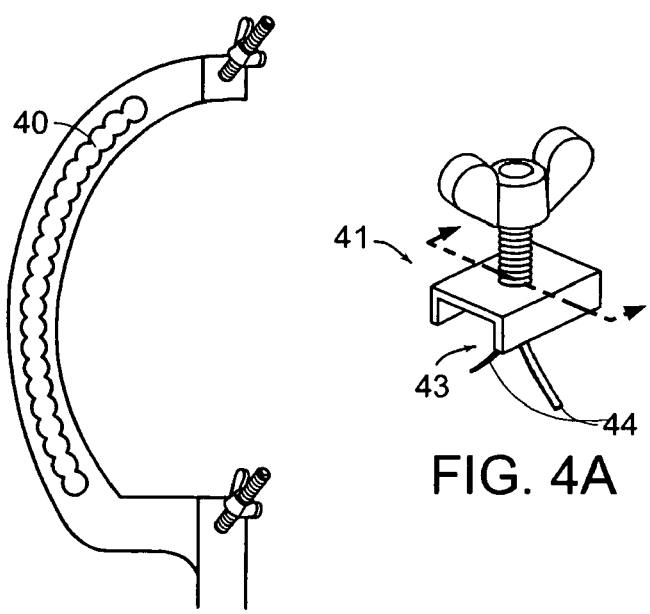
FIG. 4
FIG. 4A
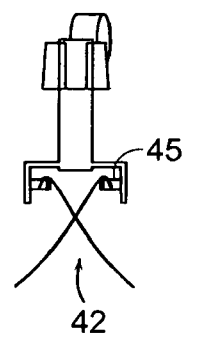
FIG. 4B

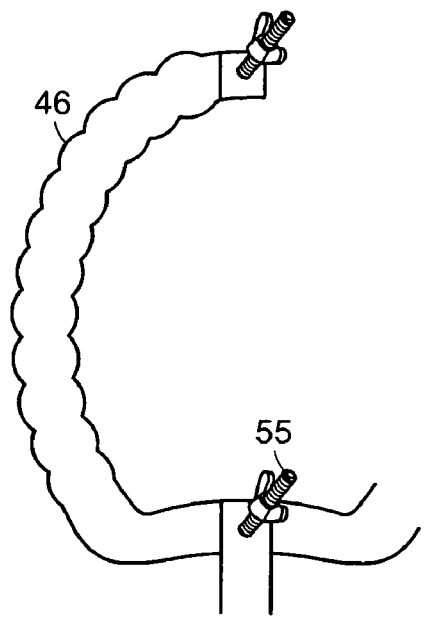
FIG. 5
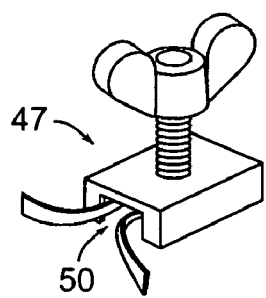 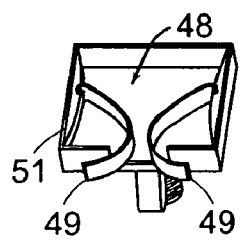 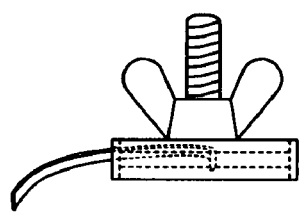
FIG. 5A  FIG. 5B  FIG. 5C

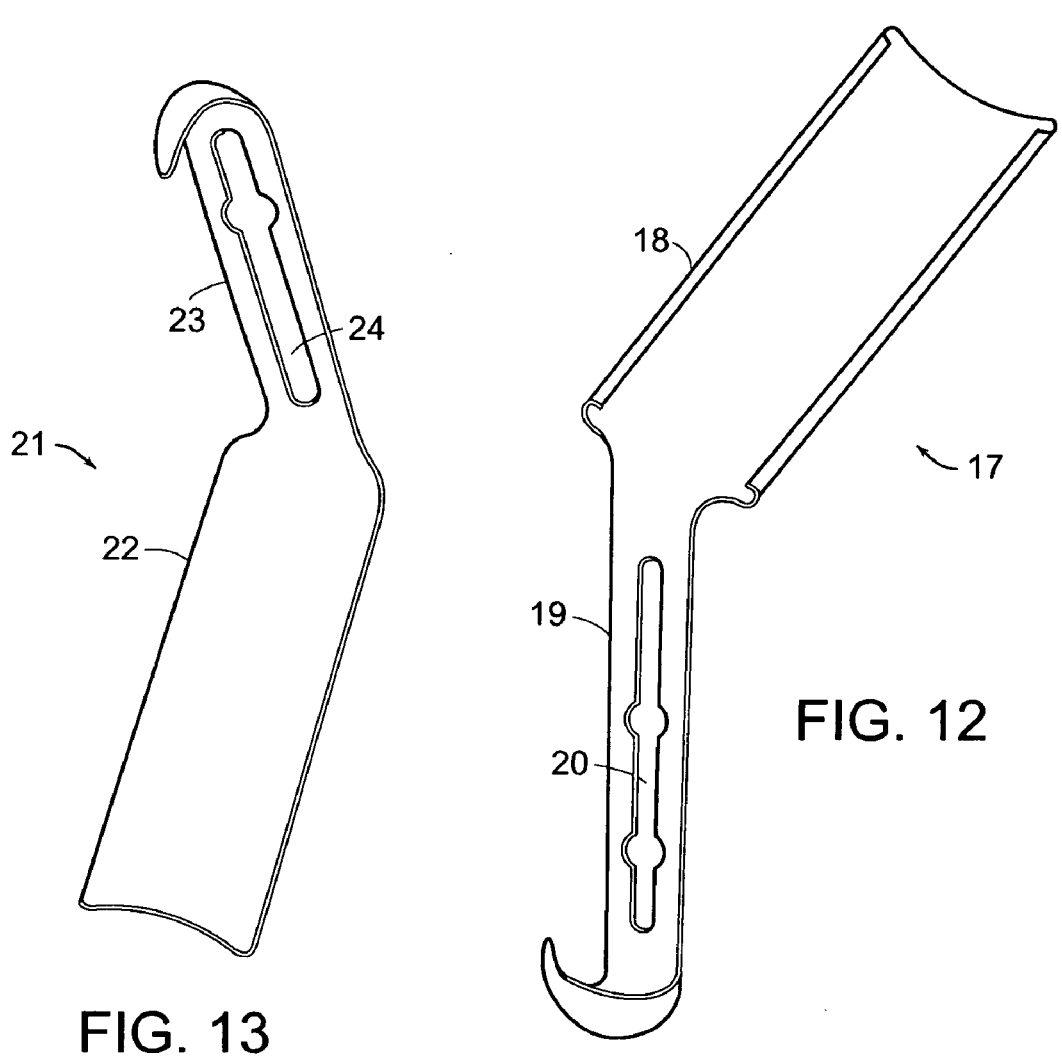
FIG. 12
FIG. 13
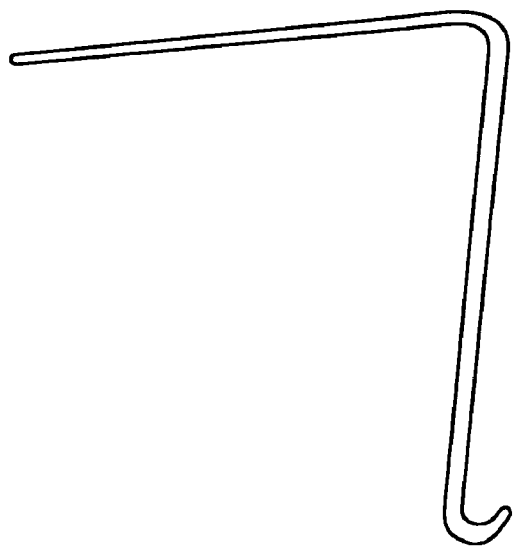
FIG. 14

SELF-RETAINING RETRACTOR

CROSS REFERENCE TO RELATED APPLICATIONS

The present application claims priority from U.S. Provisional Application, Ser. No. 60/395,234, filed Jul. 11, 2002, which is incorporated herein by reference.

TECHNICAL FIELD AND BACKGROUND ART

The invention relates to surgical devices and methods, and in particular to devices and methods for vaginal and perineal surgery.

In present techniques for vaginal surgery, it is necessary for a surgeon to be assisted by other personnel during an operation in order to retract the vaginal walls. Typically, a weight retractor is used to retract the back wall of the vagina while the assisting personnel retract the other walls of the vagina. The presence of the other personnel to assist in retraction can make the surgery more difficult by crowding the surgeon's range of motion. It may also be more costly for the surgeon, and prevent the personnel who are assisting in retraction from performing other tasks to aid in the surgery.

SUMMARY OF THE INVENTION

In an embodiment of the invention, a retraction device for gynecological procedures on a patient comprises a frame attached to a handle and at least one retractor adjustably mounted to the frame. The frame may have one or more fissures that hold suture material during a surgical procedure. The frame may be attached to the handle with a hinge. In a particular embodiment, the hinge includes a ratchet mechanism.

In another embodiment of the invention, the retraction device includes a jig for adjustably mounting the retractor to the frame. The frame of the retraction device may include a track or rail; the retractor may be mounted to the track or rail with the jig. Alternatively, the frame may include a slot, which may be corrugated, in which the jig is positioned in the slot. Another alternative includes having a portion of the edges of the frame corrugated, the jig configured to contact the edge of the frame. The jigs used in embodiments of the invention may include locks.

In an alternate embodiment of the invention, a retraction device includes a support element that is attached to the handle for retaining the device in a position. The support element may include a sheet capable of retaining the device using the weight of the patient. Alternatively, the support element may include a sheet attached to at least one rod, the rod being configured to fit into a track. A support element may also comprise a bar which is attachable to a table. A bracket or a jig may be used to attach the support element to the handle of the retraction device.

In other embodiments of the invention, a retraction device includes one or more of the retractors having a curved blade, and a retractor-handle attached to the frame. The retractor-handle may have a groove along a portion of the length of the retractor-handle; the groove having differential width in varying portions of the groove. The retractor handle may be attached to the frame with a jig. A hinge may be used to attach the curved blade to the retractor-handle. The hinge may include a ratchet-type mechanism or be configured as a ball-type hinge. The curved blade of a retractor may be configured to form a groove capable of supporting another blade. The retraction device may include an anterior retractor, a posterior retractor, or a side retractor.

According to another embodiment of the invention, a method of retracting the walls of a patient comprises: providing a retraction device including a frame, and a plurality of retractors mounted on the frame; and retracting the vaginal walls with the retractors, such that the frame maintains a separation of the retractors and the vaginal walls. The method may provide for a retraction device that includes a handle for mounting the frame in a desired position. The method may also provide for a retraction device with means of adjustably mounting the retractors on the frame.

BRIEF DESCRIPTION OF THE DRAWINGS

The foregoing features of the invention will be more readily understood by reference to the following detailed description, taken with reference to the accompanying drawings, in which:

FIG. 3 shows a frame with a groove through which a jig runs to support a retractor according to an embodiment of the invention;

FIG. 3A shows a cross-sectional view of the self-retaining retractor device of the embodiment of FIG. 3;

FIG. 4 shows a frame with a corrugated groove through which a jig runs to support a retractor according to an embodiment of the invention;

FIGS. 4A and 4B show a jig which may be used with the frame of FIG. 4;

FIG. 5 shows a frame with a corrugated edge to which a jig may attach, supporting a retractor, according to an embodiment of the invention;

FIGS. 5A–5C show a jig which may be used with the frame of FIG. 5;

FIG. 12 shows a top view of a posterior retractor for a self-retaining retractor device according to an embodiment of the invention;

FIG. 13 shows a view of a side retractor for a self-retaining retractor device according to an embodiment of the invention;

FIG. 14 shows a side view of either a side or posterior retractor for a self-retaining retractor device according to an embodiment of the invention;

DETAILED DESCRIPTION OF SPECIFIC EMBODIMENTS

Figure 1:
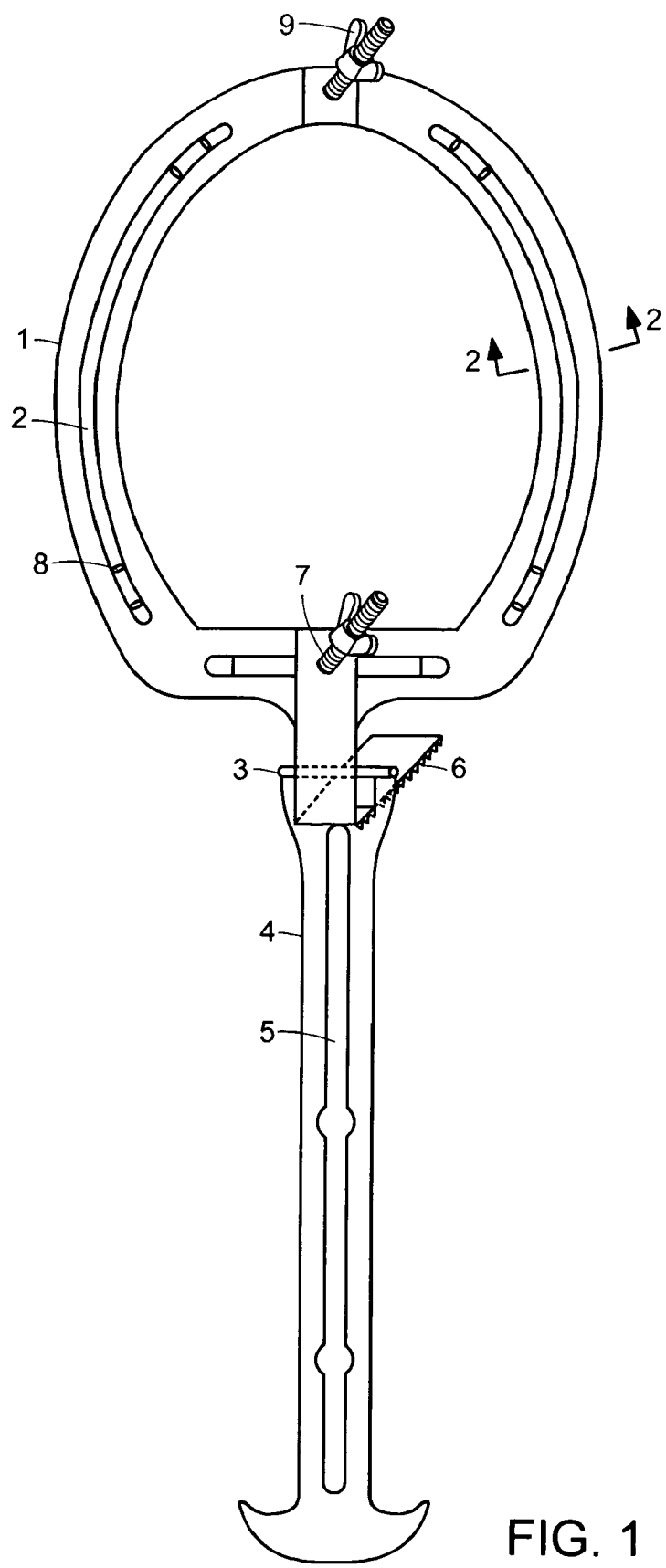
FIG. 1 shows a handle and frame of a self-retaining retractor device according to an embodiment of the invention.

FIG. 1 shows a handle and frame of a self-retaining retractor device, according to an embodiment of the invention, that removes the need for personnel to assist a surgeon in keeping the vaginal walls or perineal incision retracted, and allows for smooth, complete retraction of the side walls, with the best possible surgical field; the device may be set up by a surgeon without assistance. A racket-shaped rigid frame 1 contains a track 2 along which a surgeon may smoothly adjust the location of a set of retractors, without the need for assisting personnel. A handle 4 is connected to the frame 1 by a hinge 3, so that the frame 1 may be moved to firmly contact the patient. A ratchet mechanism 6 near the hinge allows the angle between the frame 1 and handle 4 to be adjusted, while holding the frame 1 in place against the patient. In one embodiment according to the invention, the major axis of the frame is, for example, 14 cm. in length, while the minor axis is 12 cm. in length.

Figure 2:
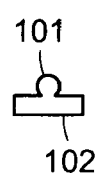
FIG. 2 shows a cross-sectional view of the frame of the self-retaining retractor of the embodiment of FIG. 1.

FIG. 2 shows a cross-sectional view of the frame of the self-retaining retractor device of the embodiment of FIG. 1. A raised portion 101 of the frame's cross-section functions as a rail, along which the surgeon may slide a set of jigs (depicted in FIG. 21) that are attached to the retractors (also discussed below). The reverse side 102 of the frame contacts the patient, and is smooth, so that the jigs for the retractor may be moved around the raised portion 101 on the reverse side of the frame without directly touching the patient.

The embodiment of FIG. 1 depicts one mechanism for mounting one or more retractors to the frame of the device. However, embodiments of the invention include any means by which a retractor may be adjustably mounted to the frame of the device, and are not limited to the use of a track or rail or jig. Several non-limiting examples are discussed herein.

FIG. 3 shows the track 2 could be substituted by a groove 35 that runs along the length of the frame. Through the groove runs a jig 36 (shown in FIG. 3A) comprised of a screw with a flat circular lower end 37 and a spring-loaded sheet of metal 38 to support its place on the groove, the upper end will be a screw and a flange-nut combination 39 to hold the different retractors.

FIG. 4 shows the track 2 could be substituted by a corrugated groove 40 that runs along the frame. Through the groove a jig 41 (shown in FIGS. 4A and 4B) comprised of a body with a cavity 42. A pin 43 at its open end holds two arms 44 in a scissors manner to engage to the dents in the grooved track 40. These arms are kept in the open position by the help of spring metals 45. A screw and flange-nut combination attached to the body may be used to hold the different retractors.

FIG. 5 shows the frame with smooth front and back surfaces, and outer and inner edges which are corrugated 46 and along which a jig may be run. The jig (shown in FIGS. 5A–5C) is comprised of a body 47 with a cavity 48 in which two parallel arms 49 held by two deferent pins 50. The two arms are kept in the retracted position by the help of metal spring 51. A screw and flange-nut combination attached to the body to hold the deferent retractors.

Persons skilled in the art will readily realize that the frame of the retraction device may take on a variety of shapes that are convenient for holding retractors during gynecological procedures; the frame is not limited to the shape shown in FIG. 1. As an example, an embodiment of the invention may include a frame, as shown in FIG. 5, that alters the frame shape to include a lower portion curved 55 into the space enclosed by the frame in order to allow retractors to be attached closer to one another.

Returning to FIG. 1, a groove 5 in the handle 4 of the retraction device allows a support element (discussed further below) to attach to the handle 4; circularly widened portions of the groove 5 allow room for a screw and flange-nut combination (shown elsewhere) to attach the support element to the handle 4. The vertical position of the retraction device during surgery may be adjusted by moving the position of the screw and flange-nut combination to different positions in the groove 5. As shown further below, a screw and flange-nut combination 7 holds the posterior retractor to the frame, while screw and flange-nut combination 9 holds the anterior retractor to the frame. As is apparent to those skilled in the art, the adjustment of the support element relative to the handle may be carried out by a variety of mechanisms, not limited to the specific embodiment described here.

Small fissures 8 in the raised portion 101 of the frame, shown in FIG. 2, may be used to allow holding of suture material for tagging or retraction, during surgery. Such fissures may, for example, contain projections that hold the suture material in position once the suture is pulled through the fissure in one direction, and from which the suture may be released when desired.

Figure 6:
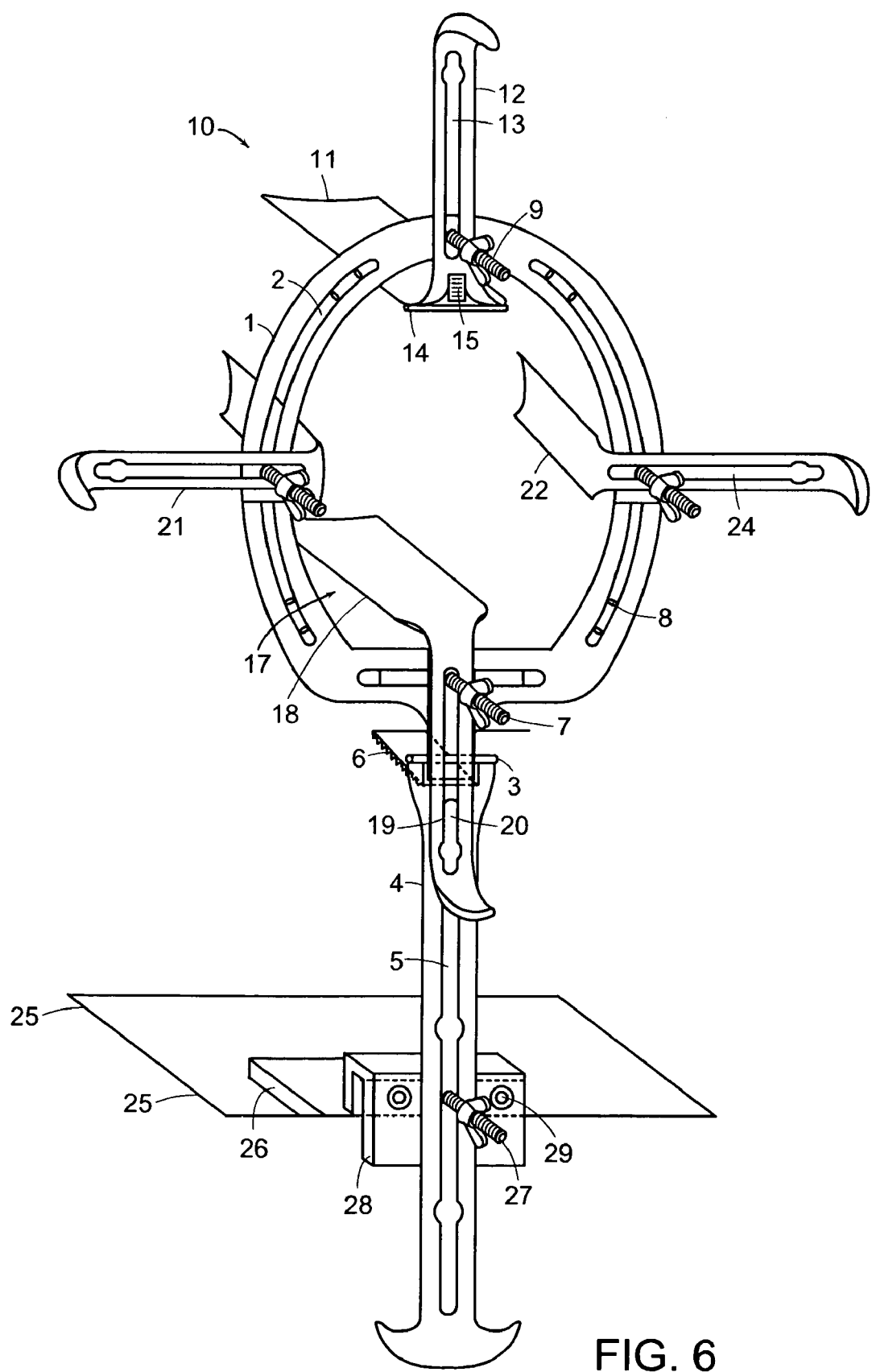
FIG. 6 shows a self-retaining retractor device with a support element to support the device using the weight of a patient according to an embodiment of the invention.

FIG. 6 shows an assembled view of a self-retaining retractor device, according to an embodiment of the invention. In the embodiment shown in FIG. 6, four movable retractors 10, 17, 21 (one on each side) are used, including an anterior retractor 10, a posterior retractor 17, and two side wall retractors 21; typically, from two to four retractors may be used, but other numbers may also be used in accordance with embodiments of the invention. Three alternative versions 25, 31, and 34 of a support element are shown in FIGS. 6, 7, 17, 18, and 19. The first version 25 of the support element allows the device to be retained in position for surgery by the patient's weight, by having support element 25 held between the patient's buttocks and the operating table. The second and third versions 31 and 34 (described later) of a support element allow the handle 4 to be attached to the operating table using the support element.

Figure 7:
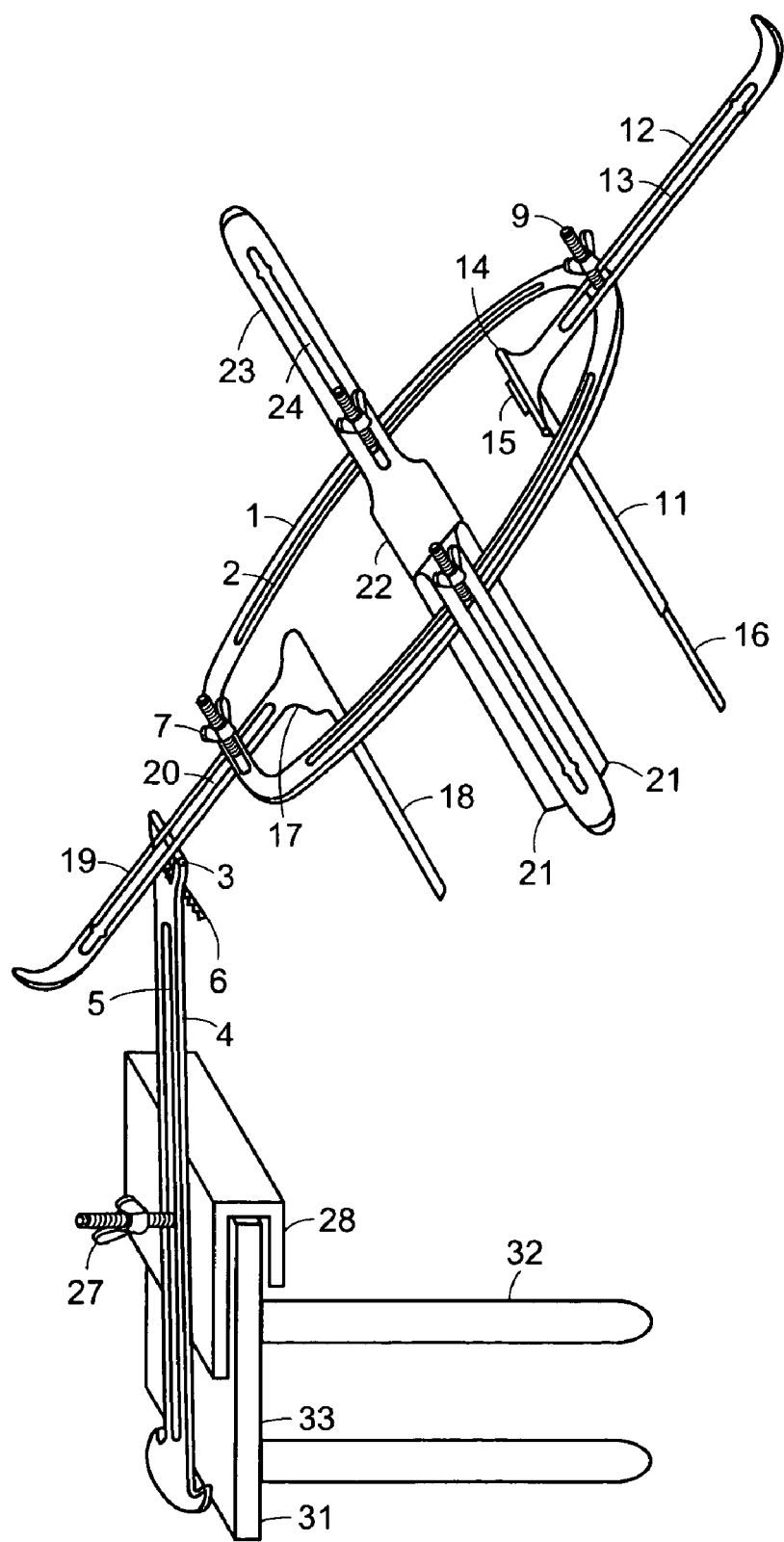
FIG. 7 shows a self-retaining retractor device with an anterior retractor having a blade supported by a curved blade and a table-mounted support element according to an embodiment of the invention.

FIG. 7 shows an oblique view of fully assembled self-retaining retractor device when utilized on patient. The view shows the retractors 10, 17, 21 fully extended and the angle of the anterior retractor open to its greatest extent. Further reference numerals indicated in FIG. 6 and 7 are discussed in each of the detailed component views of the remaining Figures.

Figure 8:
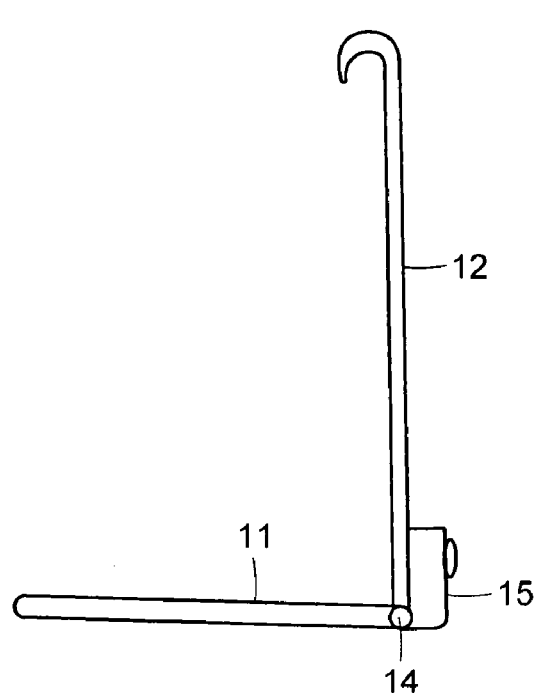
FIG. 8 shows a side view of an anterior retractor for a self-retaining retractor device according to an embodiment of the invention.
Figure 9:
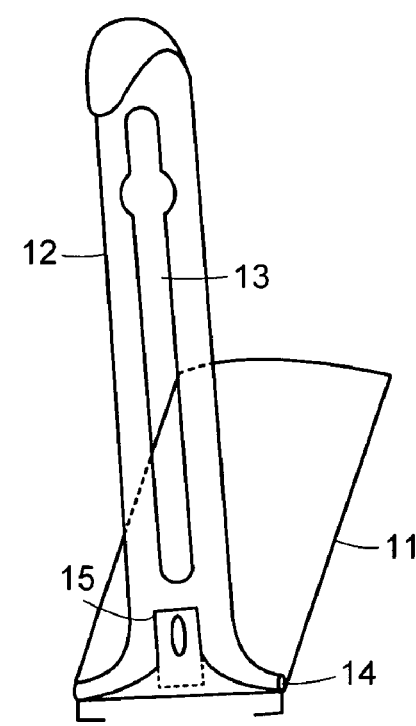
FIG. 9 shows a perspective view of an anterior retractor for a self-retaining retractor according to an embodiment of the invention.
Figure 10:
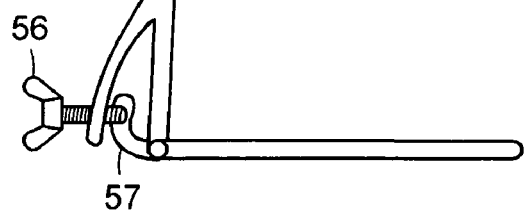
FIG. 10 shows a side view of a retractor for a self-retaining retractor device in which the blade and retractor-handle are attached with a ball-hinge according to an embodiment of the invention.

FIGS. 8 and 9 show a side view and a perspective view, respectively, of an anterior retractor 10 for a self-retaining retractor device according to an embodiment of the invention. A paddle or blade 11 of the anterior retractor has curved sides (see FIG. 3B) that allow a longer blade to be slid into the curved blade 11 as necessary during surgery. Blades of varying lengths may be utilized with the curved blade as desired. The blade 11 is attached to the anterior retractor's handle 12 by a hinge 14, which allows gentle widening of the angle of retraction according to the desire of the surgeon. A ratchet mechanism 15 allows the angle of the blade 11 with respect to the handle 12 to be adjusted, while holding the blade 11 at the chosen angle. Similar hinge and ratchet mechanisms may be used on other retractors (such as a posterior retractor or side retractor) in accordance with embodiments of the invention. Other mechanisms may also be used to hold a particular angle of the blade with respect to the handle. As another example, shown in FIG. 10, a screw and nut combination 56 may be used to attach a retractor blade to the frame with a ball type hinge 57 that allows adjustment of the angle of the retractor blade.

In a particular embodiment, a groove 13 in the handle 12 allows attachment of the anterior retractor 10 to the frame 1 using a jig (as shown in FIGS. 6 and 7), and contains an area of circular widening to allow room for a flange-nut of the jig (shown further below). The vertical position of the anterior retractor 10 may also be adjusted by moving the position of the flange-nut in the groove 13.

Figure 11:
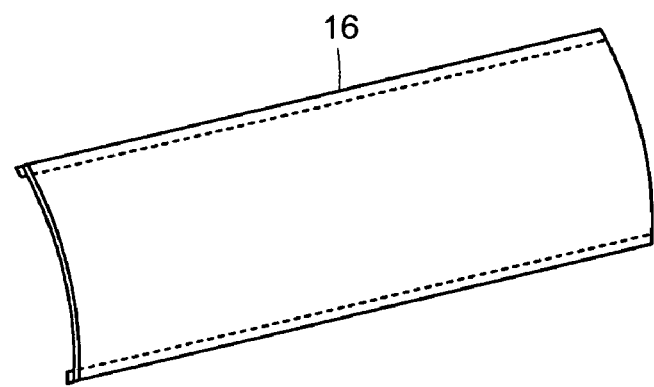
FIG. 11 shows a long blade for use with an anterior retractor according to an embodiment of the invention.

FIG. 11 shows a long blade 16 for use with an anterior retractor, in accordance with an embodiment of the invention. The long blade 16 may be inserted into the groove of the anterior retractor's blade 11 in order to give a deeper view of the surgical field. Similar blades of varying lengths may be fitted into other retractors (such as the posterior retractor 17 or side retractors 21) in accordance with embodiments of the invention.

FIG. 12 shows a top view of a posterior retractor 17 for a self-retaining retractor device according to an embodiment of the invention. The posterior retractor 17 has a curved paddle or blade 18 and a handle 19. As with the anterior retractor, a groove 20 in the handle 19 has areas of circular widening to allow room for a flange-nut of a jig (shown further below) that attaches the posterior retractor 17 to frame 1 (as shown in FIGS. 6 and 7). Groove 20 also allows for adjustment of the vertical position of posterior retractor 17. FIG. 13 shows a view of a side retractor 21 in accordance with an embodiment of the invention, which similarly features a curved paddle or blade 22, a handle 23, and a groove 24 in the handle for attachment of the retractor (as shown in FIG. 7). Groove 24 allows for adjustment of the lateral position of the side retractor 21. FIG. 14 shows a side view corresponding to either a posterior or side retractor, according to embodiments of the invention.

Figure 15:
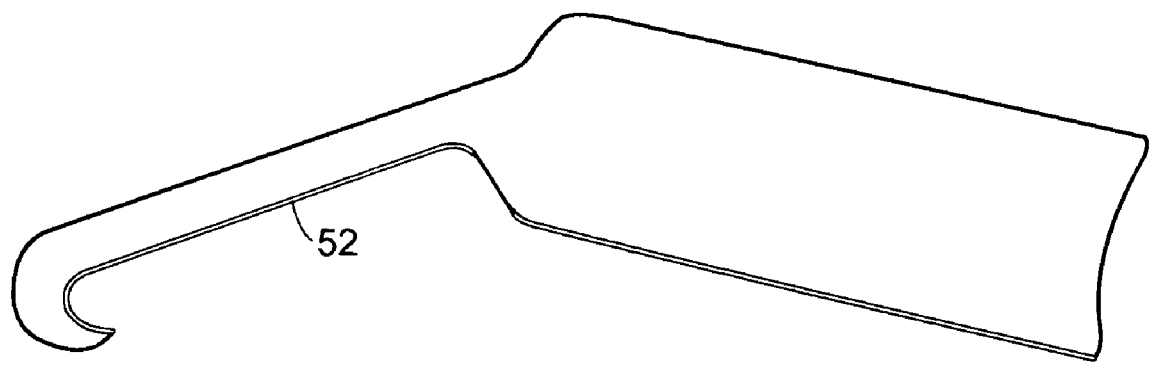
FIG. 15 shows a retractor without a slot for a self-retaining retractor device according to an embodiment of the invention.
Figure 16:
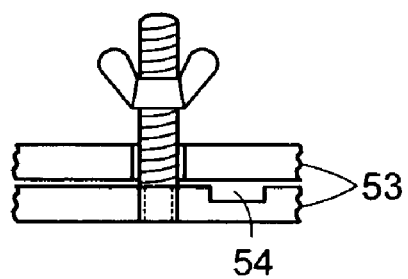
FIG. 16 shows a jig that may be used with the retractor depicted in FIG. 15.

The grooves 13, 20, 24 in the retractors 10, 17, 21 exemplify one embodiment of the invention that enables the retractors to the attached to the frame. As is apparent to those skilled in the art, other retractor designs may be used to attach the retractors to the frame in accord with embodiments of the invention. Another example, shown in FIGS. 15 and 16, depicts the retractor-handles being made of solid metal 52. Each retractor is held in place by a jig made of two sheets of metal 53. The lower sheet will have a notch 54 for attaching to the retractor. The jig described above may be used to replace any of the jigs utilized herein (e.g. jigs used with the retractor-handle, the frame handle, or support structure); a slot or groove need not be utilized when this type of jig is substituted.

Figure 17:
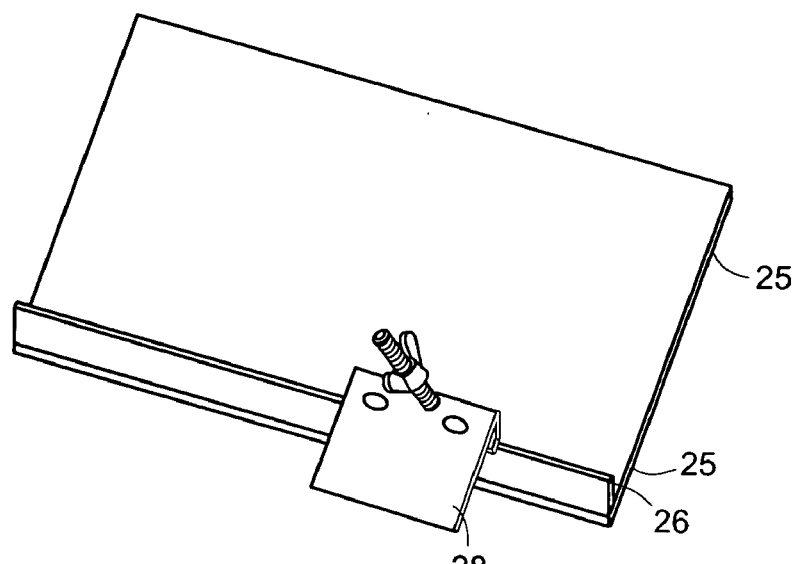
FIG. 17 shows a support element for a self-retaining retractor according to an embodiment of the invention.
Figure 20:
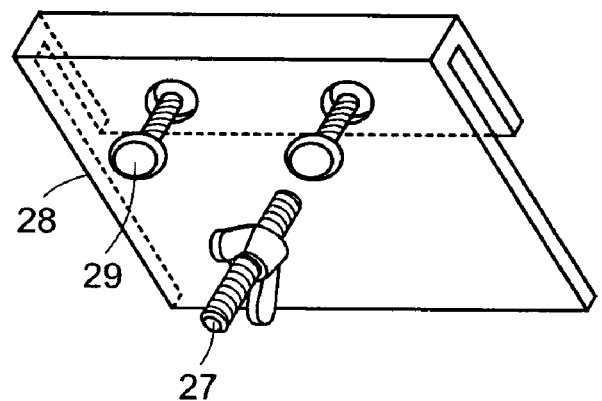
FIG. 20 shows a bracket to attach a support element to the handle of a self-retaining retractor device according to an embodiment of the invention.

FIG. 17 shows a support element 25 for a self-retaining retractor device according to an embodiment of the invention, which allows the device to be retained in position for surgery by the patient's weight, by having support element 25 held between the patient's buttocks and the operating table. Support element 25 attaches to the handle 4 (see FIG. 6). Support element 25 may be made, for example, of a stainless steel sheet, with a right angle bend 26 at its outer end. A jig, which may use a screw and flange nut combination in a similar fashion to the jigs described below in FIG. 21, allows attachment of the support element 25 to the handle 4, as shown in FIG. 17. A bracket 28 may replace the jig, as shown in FIG. 20. The bracket 28 may be made of a stainless steel metal sheet that is folded over approximately one-third of its length. The bracket 28 may be placed over the right angle bend 26. The bracket 28 may be attached to the support element 25 by screws. The bracket 28 will have a screw 29, to attach the bracket 28 to the support element 25, and flange-nut combination 27 on its front to which the handle 4 may be attached, as shown in FIGS. 6 and 20. Sterile drapes may be used to cover the right angle bend to prevent patient contact with the jig, bracket 28 or handle 4.

Figure 18:
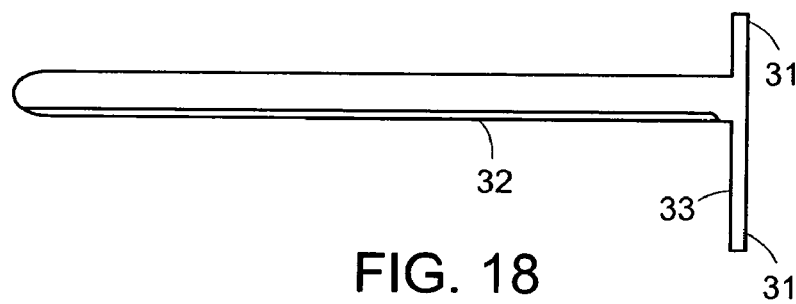
FIG. 18 shows side view of a table-mounted support element configured to fit into a cylindrical track of a table for a self-retaining retractor according to an embodiment of the invention.
Figure 18A:
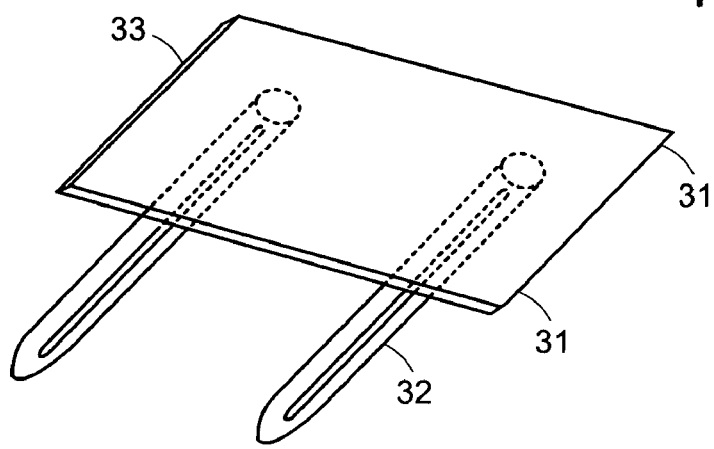
FIG. 18A shows a perspective view of the support element of FIG. 18.

FIGS. 7, 18, and 18A show an alternative table-mounted support element 31 for a self-retaining retractor device according to an embodiment of the invention. Support element 31 includes two cylindrical rods 32 (with spring type sheet on one side), attached to a sheet of metal 33. The rods 32 are configured to fit into a cylindrical track that most operating tables possess. Bracket 28 may be placed over the metal sheet after being covered by sterile drapes to secure the support element 31 to a handle 4, as described above. Alternatively, a jig may be used instead of a bracket 28, also described earlier.

Figure 19:
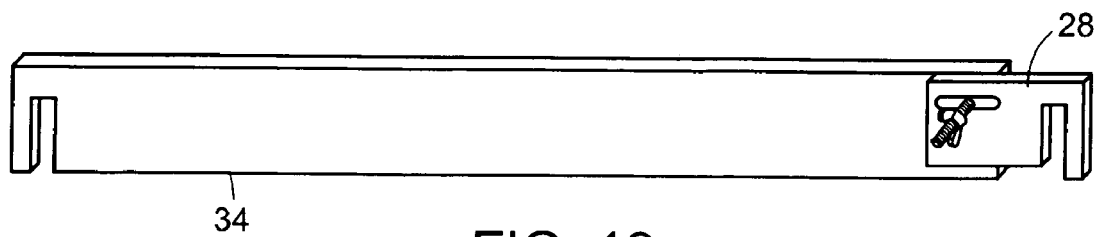
FIG. 19 shows another support element for a self-retaining retractor utilizing a bar as wide as an operating table according to an embodiment of the invention.

FIG. 19 shows another table-mounted support element 34 for a self-retaining retractor device according to an embodiment of the invention. Support element 34 includes a bar that is as wide as the operating table, and contains notches in its side members to hook to the operating table. Bracket 28 may be placed over the support element 34 after being covered by sterile drapes to secure the support element 31 to a handle 4, as described above. Alternatively, a jig may be used instead of a bracket 28, also described earlier.

Figure 21A:
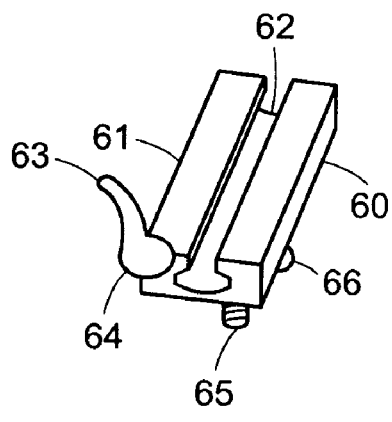
FIGS. 21A and 21B show bottom and top views of a jig for a self-retaining retractor according to an embodiment of the invention.
Figure 21B:
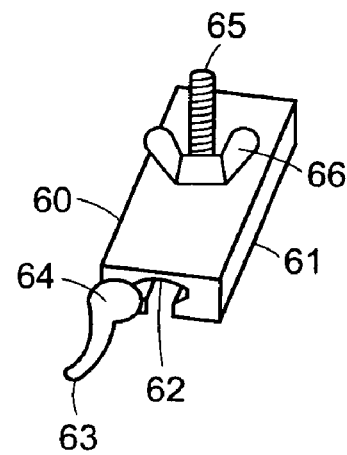
Figure 22A:
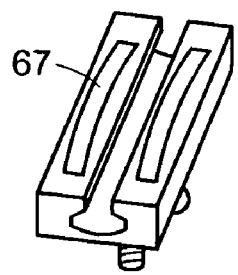
FIGS. 22A and 22B show bottom and top views of an alternative embodiment of a jig.
Figure 22B:
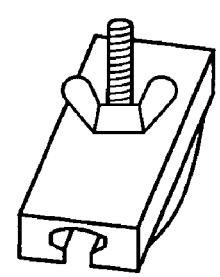

FIGS. 21A and 21B show bottom and top views of a jig 60 for a self-retaining retractor device according to an embodiment of the invention. Jig 60 may be used, for example, to movably attach retractors 10, 17, and 21 to the frame 1 (as shown in FIGS. 6 and 7), so that the retractors may be smoothly moved around frame 1 to achieve the best retraction for the surgical field. A body 61 of jig 60 contains a groove 62 that fits around the raised portion 101 (see FIG. 2) of the frame's cross-section, so that the jig 60 may slide around the frame 1. A lock 63, which may use an out-of-center wheel 64, may be used to lock the jig 60 in position on the frame 1. The lock may be used by turning the lock's handle to tighten the jig's grip on the track once the desired location for the retractor on the frame is reached. A screw 65 extends from the body 61 of the jig 60. After placing the handle groove of a retractor (such as retractor 10, 17, or 21), or groove in another component to be attached, over the screw 65, a flange-nut 66 secures the component to the jig 60. As shown in FIGS. 22A and 22B, the out-of-center wheel 64 may be replaced by two curved spring metals 67, which are attached to the lower part of the jig 60 that is in contact with the frame body 1; the spring metals 67 keeping the jig 60 in tight contact with the track, and holding the jig 60 in a desired position.

The following description provides a non-limiting example of how the self-retaining retractor device may be used. The desired support element 25, 31, 34 is placed under the patient or attached to the operating table. Sterile drapes are used to cover the patient and support element. The handle 4 is firmly attached to the supporting element 25, 31, 34 using either a jig or bracket 28, which is placed on top of the supporting element 25, 31, 34, and a screw and flange-nut combination. The position of the handle 4 is chosen to obtain the correct vertical height for the frame 1. The blade of the posterior retractor 17 may be inserted into the patient first, and then secured to the frame 1 by a screw and flange-nut combination. Then the blade of the anterior retractor 10 may be inserted, and secured to the frame; its vertical position and position on track 2 may be adjusted; and its angle may be adjusted using ratchet mechanism 15. Then the side retractors 21 may be inserted, and their lateral position and position on track 2 adjusted. However, the particular order of insertion of the retractors, as well as their positioning and angling, may be adjusted according to the nature and progress of the surgery, as will be recognized by those of skill in the art in accordance with the disclosure herein.

Although various exemplary embodiments of the invention have been disclosed, it should be apparent to those skilled in the art that various changes and modifications can be made which will achieve some of the advantages of the invention without departing from the true scope of the invention.

What is claimed is:

1. A retraction device for gynecological or perineal surgery on a patient comprising:

a one-piece frame hinged on a handle and slidably attached to a support element, the hinge allowing adjustment of the position of the handle with respect to the frame, the frame and handle requiring no assembly during the surgical procedure, the frame including a track extending along the length of the frame; and at least one retractor slidably mountable in multiple positions along the length of the track by a jig that does not contact the patient.

2. A retraction device according to claim 1 further comprising:

a ratchet mechanism for hinging the frame to the handle.

3. A retraction device according to claim 1 further comprising:

a retractor having means for holding a second blade thereby protruding farther into the surgical field.

4. A retraction device according to claim 1, wherein the track jig includes a groove for slidably mounting the jig to the track.

5. A retraction device according to claim 1, wherein the support element is a flat sheet for retaining the device in a position by the weight of the patient.

6. A retraction device according to claim 1, wherein the support element is a bar for attaching to an operating table.

7. A surgical retraction device comprising a frame with a handle and (a) one or more retractors having a blade; and (b) lengthwise positioning means for positioning retractors along a length of a frame; and (c) adjustable support means for positioning and supporting the frame adjacent to a patient; and (d) hinging means for adjusting an angle of the frame relative to the handle; and (e) widening means for adjusting an angle of a retractor relative to the frame thereby widening a surgical field;

wherein at least one retractor includes an extension means for holding a second blade thereby increasing the effective length of the retractor and the depth of the surgical field.

* * * * *